United States Patent [19]

Gotthardt et al.

[11] Patent Number: 5,016,646
[45] Date of Patent: May 21, 1991

[54] THIN ELECTRODE LEAD AND CONNECTIONS

[75] Inventors: Gerhard Gotthardt, Castle Hill; Zoran Milijasevic, Elanora Heights; Akira Nakazawa, Balmain; Michael Skalsky, Waverly, all of Australia

[73] Assignee: Telectronics, N.V., Netherlands Antilles

[21] Appl. No.: 385,990

[22] Filed: Jul. 24, 1989

Related U.S. Application Data

[63] Continuation of Ser. No. 277,419, Nov. 29, 1988, abandoned, which is a continuation of Ser. No. 38,785, Apr. 15, 1987, abandoned.

[51] Int. Cl.$^5$ ............................................. A61N 1/05
[52] U.S. Cl. ................................ 128/784; 128/785; 128/786
[58] Field of Search ........................ 128/784–786, 128/419 P, 642

[56] References Cited

U.S. PATENT DOCUMENTS

| | | |
|---|---|---|
| 3,485,234 | 12/1969 | Stevens . |
| 3,568,660 | 3/1971 | Crites et al. . |
| 3,572,344 | 3/1971 | Bolduc . |
| 3,585,707 | 6/1971 | Stevens . |
| 3,760,812 | 9/1973 | Timm et al. . |
| 3,995,623 | 12/1976 | Blake et al. ............... 128/642 |
| 4,131,759 | 12/1978 | Felkel . |
| 4,135,518 | 1/1975 | Dutcher . |
| 4,172,451 | 10/1979 | Kline . |
| 4,236,529 | 12/1980 | Little ............... 128/785 |
| 4,280,511 | 7/1981 | O'Neill ............... 128/784 |
| 4,369,794 | 11/1983 | Furler . |
| 4,402,328 | 9/1983 | Doring ............... 128/785 |
| 4,444,195 | 4/1984 | Gold ............... 128/786 X |
| 4,499,907 | 2/1985 | Kallok ............... 128/786 |
| 4,559,951 | 12/1985 | Dahl et al. ............... 128/642 |
| 4,590,950 | 5/1986 | Iwaszkiewicz ............... 128/786 |

FOREIGN PATENT DOCUMENTS

| | | |
|---|---|---|
| WO04182 | 12/0383 | PCT Int'l Appl. . |
| 8002231 | 10/1980 | PCT Int'l Appl. ............... 128/786 |

Primary Examiner—Lee S. Cohen
Attorney, Agent, or Firm—Finnegan, Henderson, Farabow, Garrett & Dunner

[57] ABSTRACT

A body implantable electrode lead including a connector structure for enabling connection with an outermost conductor of the lead is disclosed. The implantable lead is of a multilayer configuration, being covered by an insulating biocompatible sheath. An annular section of the outer sheath is removed to expose a corresponding annular section of the outermost conductor of the lead. The exposed conductor section can be used as an electrode either directly or by attaching a conductive electrode ring via swaging, a conductive adhesive or the like.

7 Claims, 9 Drawing Sheets

THIN ELECTRODE LEAD AND CONNECTIONS

This application is a continuation, of application Ser. No. 277,419, filed Nov. 29, 1988, now abandoned, which is a continuation of application Ser. No. 038,785, filed Apr. 15, 1987 and now abandoned.

BACKGROUND OF THE INVENTION

1. Field Of The Invention

The present invention relates to the field of implantable bipolar or multipolar electrode leads and, more particularly, to a structure for providing electrical connection with one of a plurality of conductors in such leads.

2. The Prior Art

Permanent implantable multiple conductor electrode leads are well known in the art and are used for a variety of purposes. A common use of such leads is in connection with pacemakers in which the lead is connected at a proximal end to a pacemaker, and has a distal end implanted in the heart for appropriate stimulus. Such a lead may simultaneously provide for monitoring of body function through additional conductors separate from those used to carry pulses generated by the pacemaker. However, a problem has arisen in balancing the benefits of multiconductor electrode leads with their larger diameters against the benefits of using as small a diameter lead as possible so as to facilitate ease of passage through and implantation in the body.

A further problem arises with respect to providing electrical connection between the implantable lead and proximal or distal tips. It is known to provide swaged connectors which may also include an auxiliary support, such as tubing. Of course, bipolar and multipolar leads require two or more such swaged conductors. Such a construction, however, tends to render the electrode lead thick and bulky compared to the veins through which it must pass.

As the number of conductors within the lead increases, so does the bulk of the resultant lead. Attempts have been made to render the lead, itself, conductive so as to eliminate the need for discrete connectors. Nevertheless, a need remains for an implantable electrode lead having a plurality of both implantation in the body and conductors yet permitting ease of connection to other structures. This need is particularly strong in the case of multiconductor leads, such as bipolar electrode leads for cardiac pacemakers.

SUMMARY OF THE INVENTION

Accordingly, it is an object of the invention to provide an implantable electrode lead having multiple conductors and a small diameter connector.

It is another object of the present invention to provide connection with multiconductor electrode leads without adding to the diameter or bulk of such leads.

A further object of the present invention is to provide a connector for a multiconductor lead which is sealed against infiltration by body fluids and the like.

Additional objects and advantages of the present invention will be set forth in part in the description that follows and in part will be obvious from the description or may be learned by practice of the invention.

To achieve the objects and in accordance with the purpose of the invention as embodied and as broadly described herein, a body implantable electrode lead is provided which comprises: a first layer of non-conductive material forming an elongated tube; a plurality of layered conductors wound about the first layer, the outermost one of the plurality of conductors comprising a first conductor and a second layer of body-compatible non conductive material formed over the plurality of conductors and the first layer, with an annular portion of the second layer having been removed to expose a section of the first conductor and facilitate electrical connection therewith. The exposed section of the first conductor can be used as a ring electrode, itself, or a discrete ring electrode may be provided affixed thereto and sealed against invasion of body fluids.

The accompanying drawings, which are incorporated in and constitute a part of this specification, illustrate presently preferred embodiments of the invention and, together with the description, serve to explain the principles of the invention.

DESCRIPTION OF THE PREFERRED EMBODIMENTS

Reference will now be made in detail to the presently preferred embodiments of the invention, examples of which are illustrated in the accompanying drawings. Throughout the drawings, like reference characters are used to designate like elements.

Figure 1:
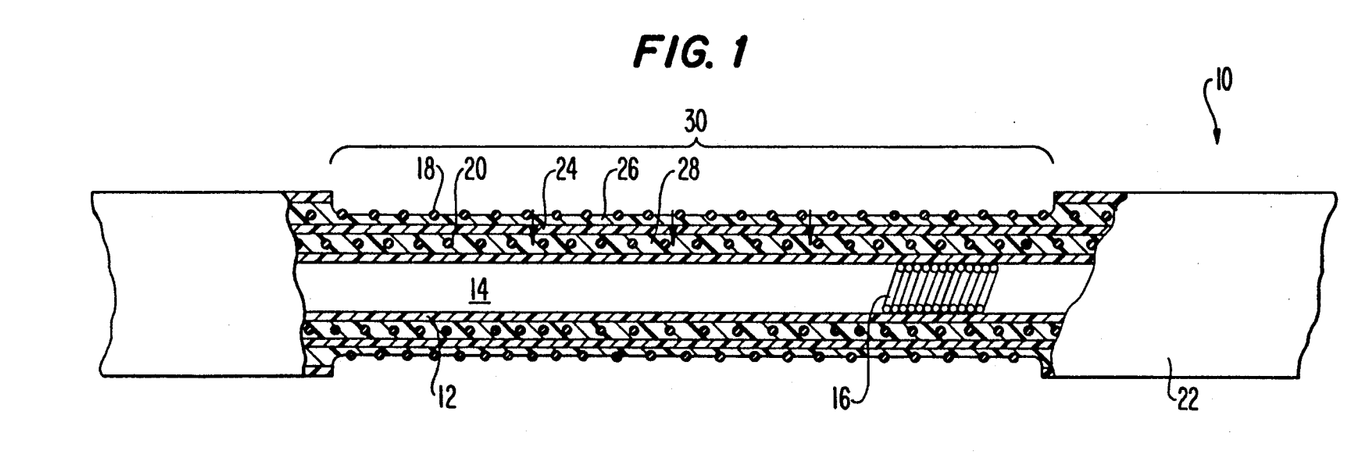
FIG. 1 is a cross-sectional view of an implantable electrode lead according to the present invention.

FIG. 1 is a cross-sectional view of a portion of a body implantable electrode lead 10 which incorporates the teachings of the present invention. While it is to be understood that electrode lead 10 has a proximal end, which can be connected to a cardiac pacemaker or other circuitry, and a distal end, which is suitable for implantation in the body, these are not illustrated in FIG. 1 since their disclosure is not necessary to understand the invention.

In the illustrated lead, a first layer of non-conductive material forming an elongated tube is provided. As embodied in FIG. 1, a first layer 12 is shown by way of example. Layer 12 is preferably comprised of polyurethane or a similar insulation material. Layer 12 may also be provided with a lumen 14 to permit passage of fluids or to provide for a conductor, such as a helically wound coil 16.

A plurality of layered conductors are provided disposed about the first layer, the outermost one of the plurality of conductors comprising a first conductor. In the embodiment of FIG. 1, a plurality of layered conductors 18 and 20 are illustrated. Both conductors 18 and 20 are wound in a regularly disposed coil-like fashion about first layer 12. Conductors 18 and 20 are preferably made of a conductive material such as platinum, platinum/iridium alloy, tungsten, copper, gold, silver, MP35N, titanium, carbon, stainless steel or a composite or mixture of these or other materials. In the illustrated embodiment of FIG. 1, conductor 18 may be considered to be a "first conductor" as that term is used in the claims, since conductor 18 is the outermost conductor relative to the group of layered conductors 18, 20. Although only two conductors are illustrated in FIG. 1, it should be appreciated that more conductors can be provided without departing from the spirit or scope of the invention.

A second layer of body-compatible non-conductive material is provided formed over the plurality of conductors and the first layer. As shown in FIG. 1, a second layer 22 is provided over conductors 18, 20 and first layer 12. Preferably, layer 22 is a polyurethane coat that can be readily cut. Other biocompatible material suitable for these purposes are known in the art and need not be described in detail for purposes of understanding the present invention.

As can be appreciated from FIG. 1, conductors 18, 20 are provided in a multilayer fashion, with each one being separated from the other by an insulating layer 24. This insulating layer 24 can be of a material similar to that of first layer 12 or other suitable insulating material. Additionally, since conductors 18, 20 are provided in a coiled fashion, each conductor is embedded within a respective intermediate silicone layer 26, 28. This arrangement ensures stability of the conductors and contributes to overall strength of the lead.

It should be appreciated that the number of layers of conductors and corresponding insulation can easily be increased to any desired number. It should also be appreciated that various types of "conductors" can be employed, at least with respect to interior conductors such as coil 16, other than electrical conductors; for example, chemical or optical means such as tubes and optical fibers, could be used. Such modifications are considered within the scope and spirit of the present invention.

Means for manufacturing such a lead, including coiled multilayered conductors, is disclosed in P.C.T. Berkley application Ser. No. US83/00827 which was published on Dec. 8, 1983 under Publ. No. WO 83/04182. The Berkley application is hereby expressly incorporated herein by reference.

According to the invention, an annular portion of the second layer is removed to expose a section of the first conductor and facilitate electrical connection therewith. As shown in FIG. 1, a portion of layer 22 has been removed, leaving a correspondingly annular exposed section 30 of the first conductor 18. Such removal can be accomplished by cutting and stripping of layer 22. In so doing, it is noted that intermediate silicone 26 is also removed to a depth sufficient to expose first conductor 18. According to another method of construction, exposed section 30 can be formed concurrently during manufacture of the electrode lead, e.g., either by not forming the overlying insulation material from the outset or by removing it during the manufacturing process.

According to a presently preferred embodiment, exposed section 30 is approximately 6 mm in length, although this dimension is subject to variations depending upon the particular application of the lead, for example. To expose first conductor 18, it is necessary to remove all of layer 22 within section 30; however, layer 26 need not be fully removed, but instead only partially removed to a depth sufficient to expose conductor 18. In the alternate construction method disclosed above, layer 26 could instead be only half formed, i.e., deposited to half or other sufficient depth, suitable for leaving conductor 18 exposed within section 30.

The exposed section 30 is used to provide electrical connection between first conductor 18 and, for example, the body tissue in which the lead has been implanted. This can be accomplished either directly, i.e. through use of the first conductor 18 itself, or through an intermediate ring electrode as described further below.

Figure 2:
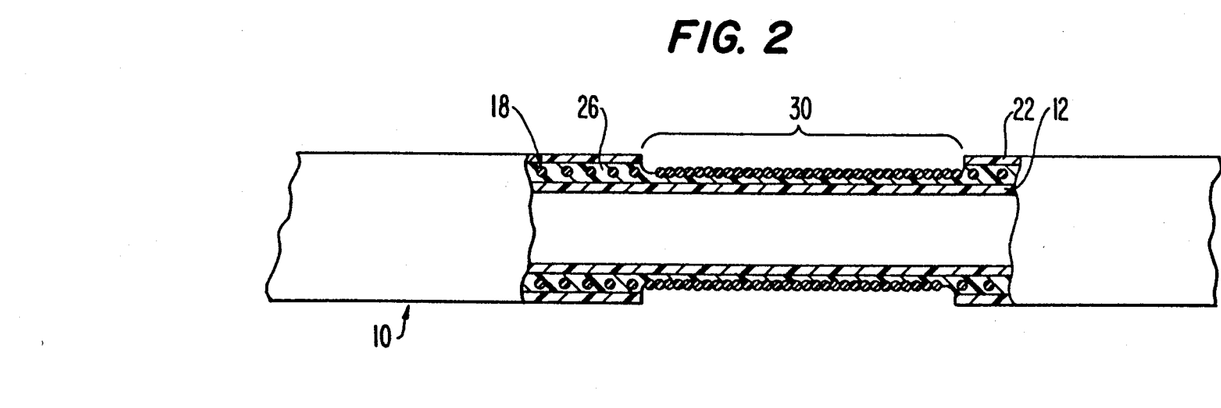
FIG. 2 is a cross-sectional view of an implantable electrode lead of the present invention in which the first conductor is closely wound to form a ring electrode.

FIG. 2 illustrates an embodiment in which first conductor 18 has a small pitch throughout exposed section 30. That is, the pitch of first conductor 18 in the sections of electrode lead 10 still covered by layer 22 is greater than that within exposed section 30. Preferably, the coils of first conductor 18 are wound so as to actually contact one another within exposed section 30 whereby conductor 18 effectively comprises a ring electrode within region 30. A method and apparatus for changing the pitch in a coiled conductor of an electrode lead is described in the aforementioned Berkley PCT application.

The embodiment illustrated in FIG. 2 is highly desirable in that the diameter of section 30 where electrical connection is made is actually smaller than that of the other portions of the electrode lead. This is directly opposite to typical prior art arrangements in which the electrical connection portion is of a greater diameter than the electrode lead.

Figure 3:
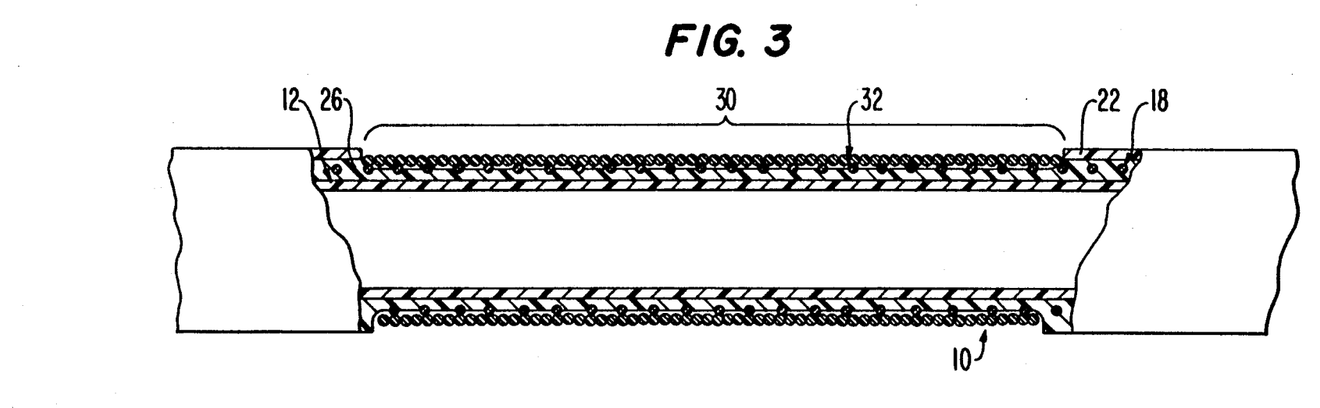
FIG. 3 is a cross-sectional view of an implantable electrode lead of the present invention in which a separate coiled conductor is provided as a ring electrode.

Another embodiment of the present invention is shown in FIG. 3, in which a second conductor 32 is provided coaxially about an exposed section 30 of first conductor 18. Conductor 32 may comprise material similar to that of first conductor 18 and is preferably tightly coiled so as to form an effective electrode ring. By drawing second conductor 32 tightly into contact with first conductor 18 within exposed section 30, electrical contact between conductors 18 and 32 is ensured. Second conductor 32 may be provided by means of coiled wire, ribbon, mesh or other suitably shaped material to electrically engage first conductor 18.

Figure 4:
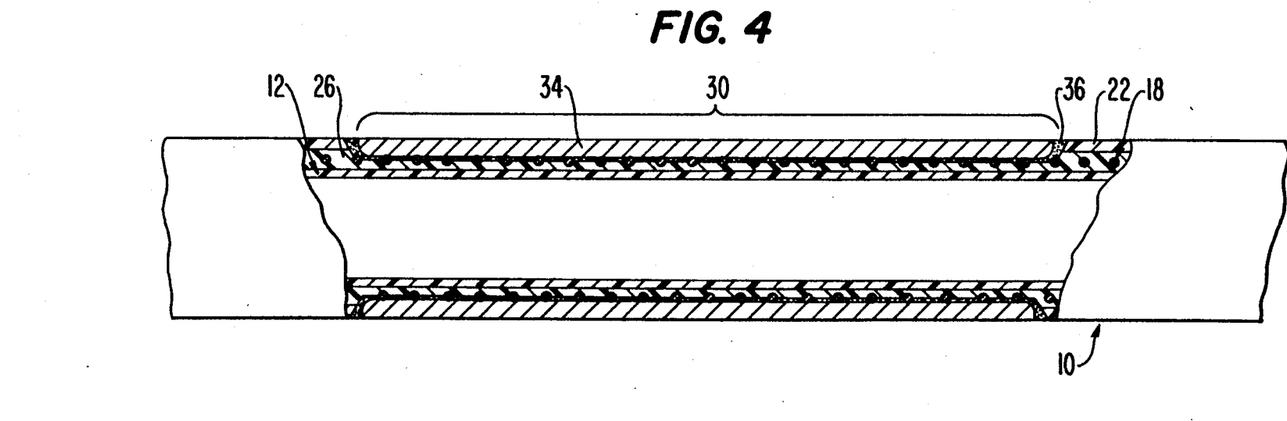
FIG. 4 is a cross-sectional view of an implantable electrode lead of the present invention showing a swaged electrode ring.

Another embodiment of a second electrode according to this invention is illustrated in FIG. 4, in which a second conductor is designated by reference character 34. According to this embodiment, second conductor 34 is a conductive ring that is swaged in place contacting first conductor 18. Through use of swaging techniques that are well known in the art, electrode lead 10 can be passed through the conductive ring forming second conductor 34 until the ring is positioned over exposed section 30. Thereafter, the ring can be swaged so as to force it into electrical and mechanical contact with first conductor 18.

Preferably, the ring comprising second conductor 34 is formed of a conductive material such as platinum. Ring 34 may further be fixed in place by means of an adhesive 36 which serves to smooth out the surface of the overall electrode lead and prevents the ingress of fluids underneath the ring. Biocompatible adhesives suitable for such purposes are well known in the art and need not be described further.

Figure 5:
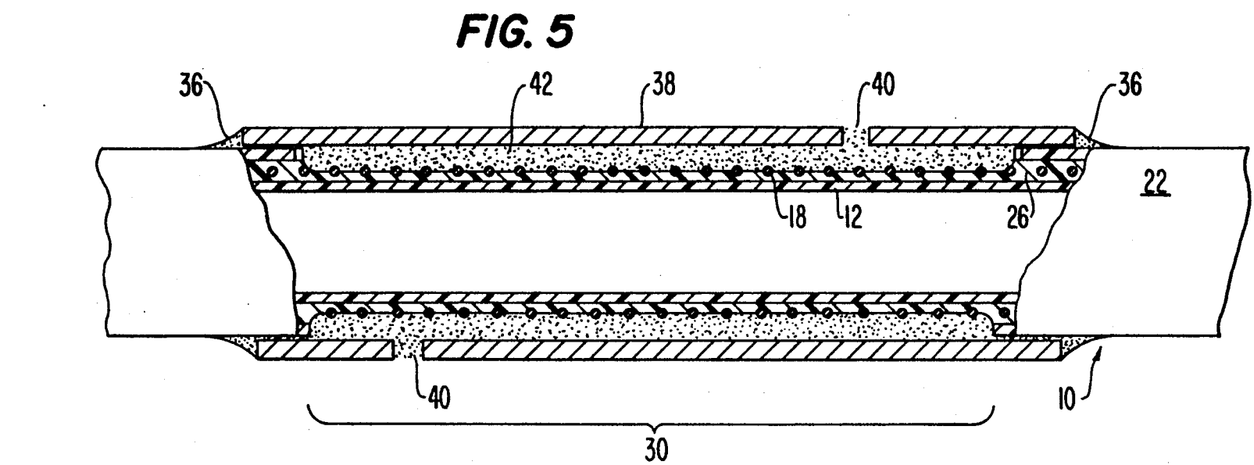
FIG. 5 is a cross-sectional view of another implantable electrode lead according to another embodiment of the present invention.
Figure 6:
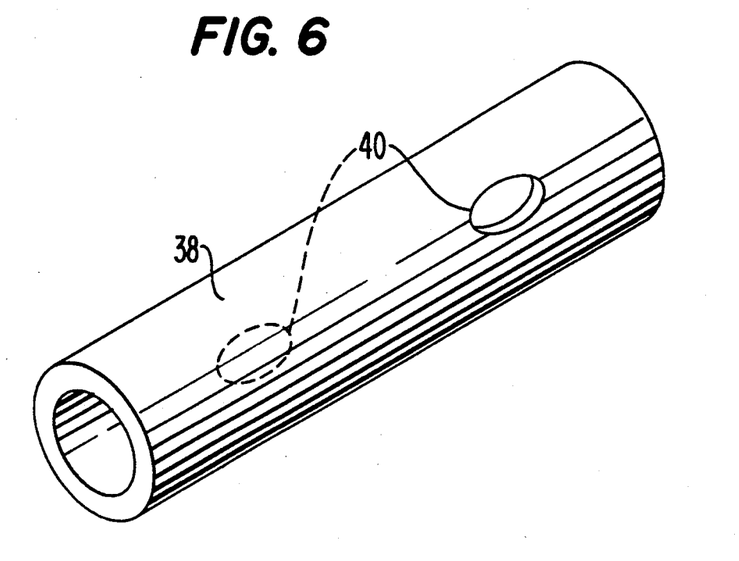
FIG. 6 is a perspective view of a ring electrode for use with the lead of FIG. 5.

Another embodiment of an implantable electrode lead having a connector as illustrated in FIGS. 5 and 6 will now be described. According to this embodiment of the invention, a conductive ring is positioned coaxially over the exposed section of the first conductor and over the edges of the second layer adjacent the exposed section. As illustrated in FIG. 6, by way of example, a conductive ring 38 is formed of a conducting material, such as platinum. Ring 38 has an internal diameter of a size sufficient to permit electrode lead 10 to pass therethrough. As shown best in FIG. 5, the length of ring electrode 38 is slightly greater than that of exposed section 30, such that ring 38 also covers the edges of second layer 22 immediately adjacent exposed section 30.

Ring electrode 38 is provided with two diametrically opposed holes 40. Once ring 38 is positioned coaxially over exposed section 30, a conductive adhesive 42 is introduced into the void between ring electrode 38 and first conductor 18 via holes 40. Preferably, this is done by injecting adhesive 42 through one hole and permitting it to exit via the other hole. Suction can be enlisted to assist this procedure. Adhesive 42 is conductive and is preferably biocompatible so as to provide both electrical and mechanical coupling between ring electrode 38 and first conductor 18. For example, adhesive 42 may be silicon rubber filled with a biocompatible conductive powder, such as platinum, carbon or the like.

To further strengthen the mechanical attributes of ring electrode 38, it may be affixed to second layer 22 via adhesive 36 of a type described previously. This arrangement also serves to ensure sealing of the entire connector and to prevent ingress of body fluids.

Figure 7:
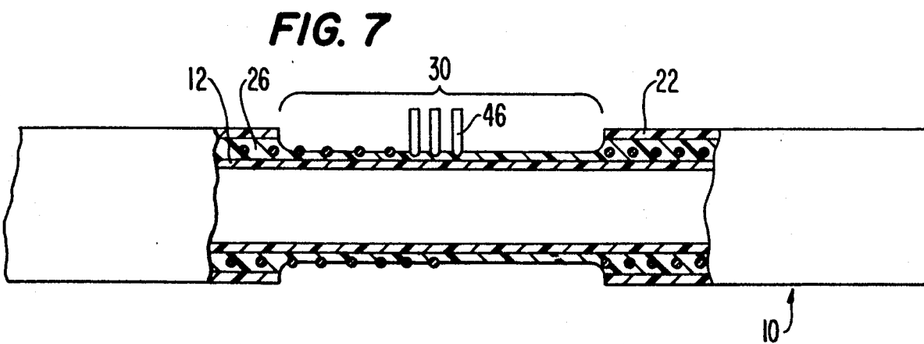
FIG. 7 is a cross sectional view of an implantable electrode lead according to a further embodiment of the present invention.
Figure 8:
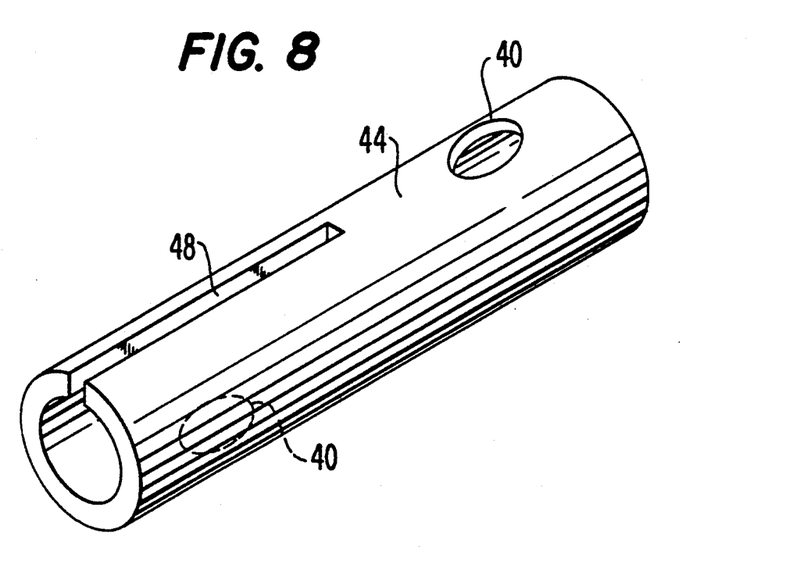
FIG. 8 is a perspective view of an electrode ring for use with the lead of FIG. 7.
Figure 9:
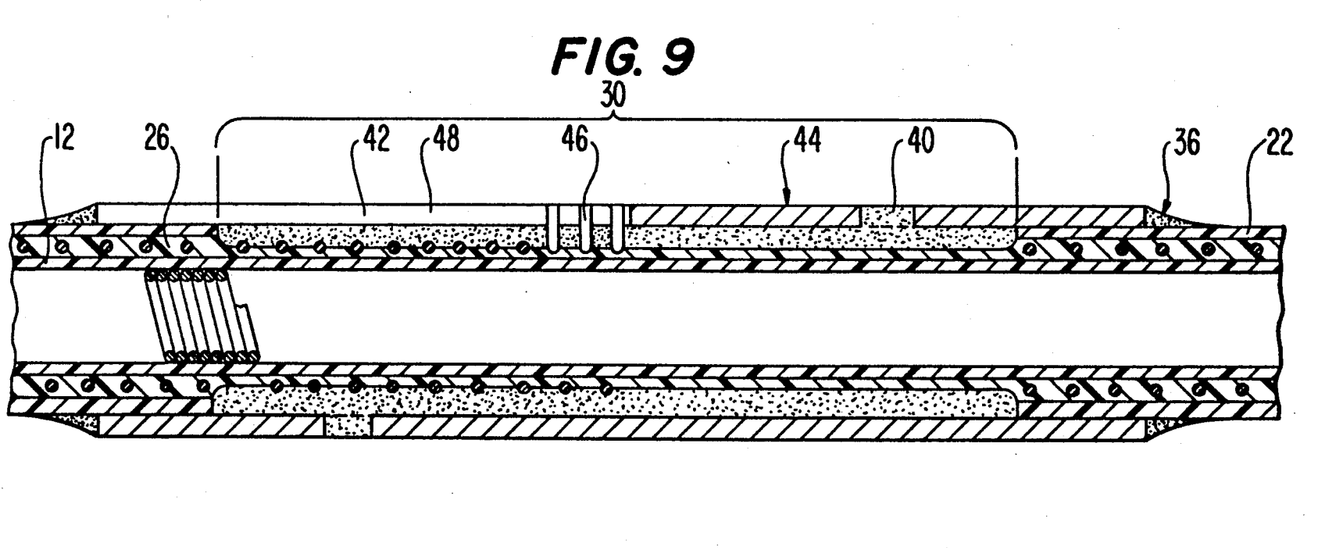
FIG. 9 is a cross-sectional view showing the lead of FIG. 7 with the ring of FIG. 8 in place.

Another embodiment of the present invention is illustrated in FIGS. 7-9. According to this embodiment, a conductive ring is positioned coaxially over the exposed section of the first conductor and over the edges of the second layer adjacent the exposed section, with the first conductor being partially unwound and disposed in a slot formed in the ring so as to facilitate electrical connection. As illustratively shown in FIGS. 7-9, a conductive ring is of a construction similar to that described above with respect to ring 38, with diametrically opposed holes 40. However, ring 38 has a longitudinal slot 48. First conductor 18 is cut and partially unwound within exposed section 30, resulting in a plurality of radially disposed aligned ends 46. Ring 44 is slid over electrode lead 10 such that the exposed conductor ends 46 are introduced into slot 48. Mechanical and electrical connection between ring 44 and the first conductor 18 can be accomplished by welding, swaging, or otherwise compressing ring 44 so as to firmly encapture exposed ends 46. Alternately, or in addition to these mechanical coupling arrangements, the void between ring 48 and first conductor 18 can be filled with a conductive adhesive 42, as illustrated best in FIG. 9. To accomplish this filling, holes 40 are used in the same manner as described above. Additionally, a biocompatible adhesive 36 can be used to seal the ends of ring 42 to outer layer 22 in the manner described above.

Figure 10:
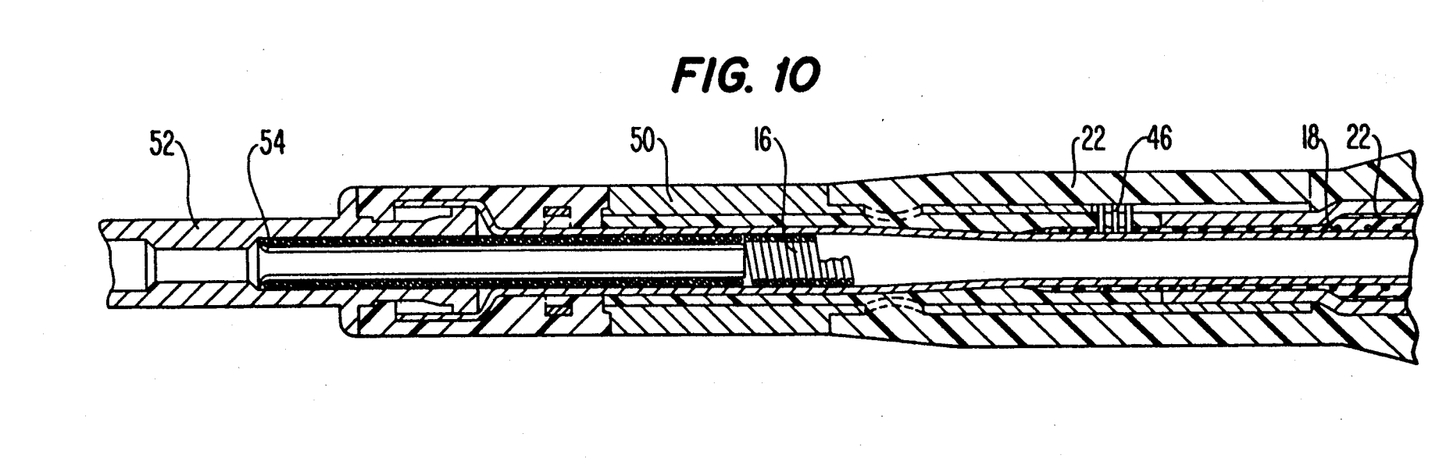
FIG. 10 is a cross-sectional view of a proximal electrode tip coupled to a lead incorporating the teachings of the present invention.

FIG. 10 illustrates a proximal connector affixed to an electrode lead by means of a ring electrode as described above with regard to FIGS. 7-9. A bipolar arrangement is illustrated in the drawing, including a proximal ring 50 and a proximal pin 52. Ring 50 is electrically connected to first conductor 18 by means of a conductive ring of the type described above with respect to FIGS. 5-6 or FIGS. 7-9. Proximal pin 52 can be coupled to inner helix 16 by first placing a support pin 54 centrally within helix 16 and then swaging proximal pin 52 thereover. This arrangement causes helix 16 to be tightly trapped between pins 52, 54. The overall configuration of a proximal connector suitable for connecting an implantable electrode lead with other apparatus is well known and need not be described in further detail for purposes of this invention.

Figure 11:
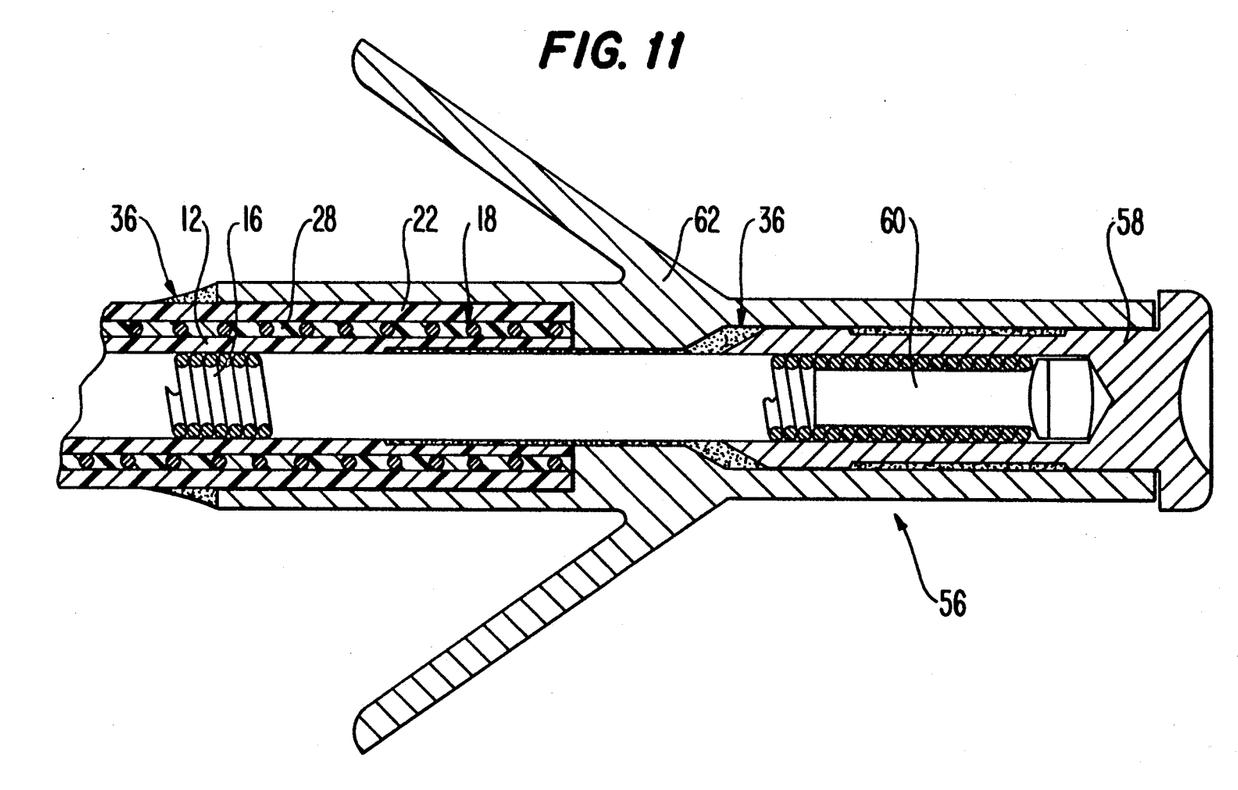
FIG. 11 is a cross-sectional view of a distal electrode tip coupled to a lead incorporating the teachings of the present invention.

A distal tip electrode for use with an electrode lead incorporating the teachings of the present invention is shown in FIG. 11 and is generally designated by reference character 56. Distal electrode 56 is designated for use with a corresponding ring electrode (not shown) of a type described above. Thus, since this ring electrode is coupled to first conductor 18, distal electrode 56 is typically coupled to inner helix 16. As shown in FIG. 11, distal electrode 56 comprises a distal tip 58 swaged over a pin 60 positioned inside inner helix 16. Through this arrangement, distal tip 58 is brought into electrical contact with inner helix 16. To complete the assembly, a tine structure 62 is glued over electrode tip 22 via a biocompatible adhesive 36. The trailing end of tine assembly 62 is also preferably sealed with biocompatible adhesive 36.

In known fashion, distal tip 22 is preferably made of a biocompatible conducting material such as platinum, platinum/iridium alloy or the like, while support pin 60 can be made from a variety of suitable conducting materials.

Figure 12A:
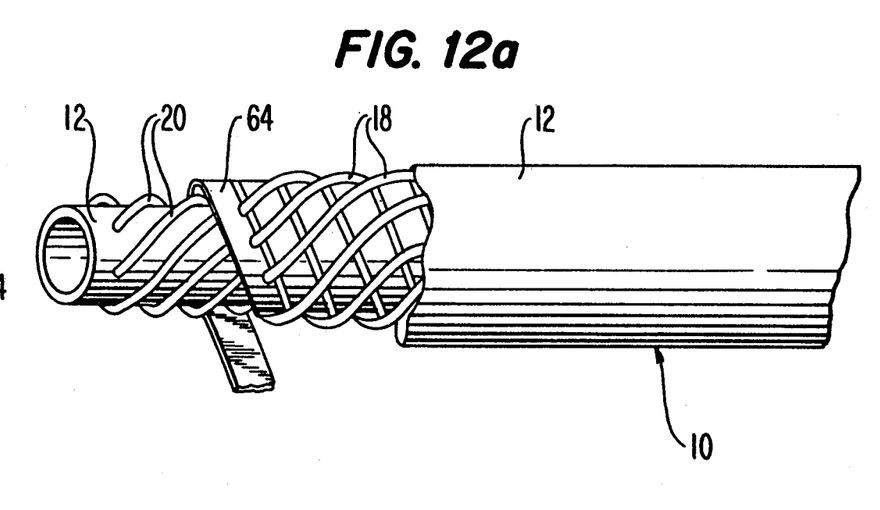
FIGS. 12a and 12b are, respectively, perspective and cross-sectional views of a multiconductor electrode lead usable with the present invention.
Figure 12B:
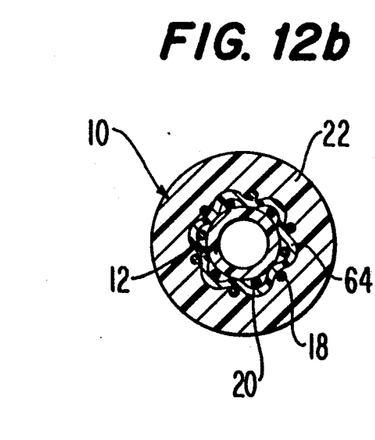

FIGS. 12a and 12b illustrate another type of multiconductor cable which can be used according to the present invention. In this cable, a multiconductor electrode lead is provided in which an inner conductor 20 is helically wound about a first insulating layer 12, with an outer conductor 18 helically wound about both. An intermediate insulating sheath 64 separates the inner and outer conductors 18, 20, while an outer insulation sheath 22 covers the entire assembly. Material suitable for these purposes has been described above.

As shown in FIGS. 12a and 12b outer conductor 18 may be helically wound about inner conductor 20 so that the former is in the interstices formed between the later. By cutting through a portion of outer layer 22 so as to expose an annular section of inner conductor 18, the foregoing electrode structures can be utilized to facilitate connection to the outer conductor 18.

Figure 13:
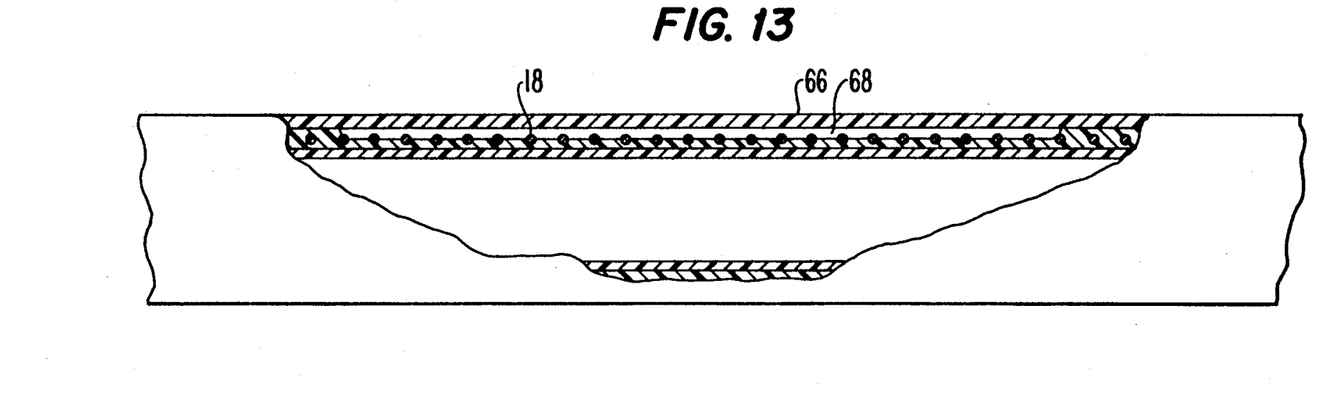
FIGS. 13 and 14 are, respectively, cross-sectional and perspective views illustrating a commercially preferred embodiment of an electrode lead incorporating the teachings of the present invention.
Figure 14:
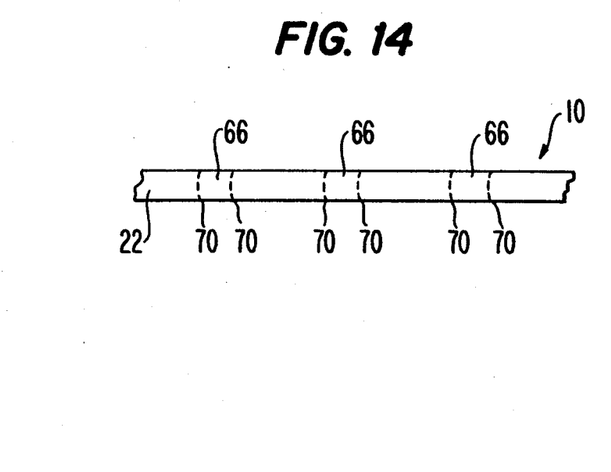

Another embodiment of an electrode lead according to the present invention is illustrated in FIGS. 13 and 14, with particular emphasis being placed on providing a commercially desirable product. FIG. 13 illustrates details of an electrode lead for use with a connector of the type illustrated and referred to throughout the foregoing drawings and description, including an exposed portion 30 in which insulation has been removed from first conductor 18. In the embodiment illustrated in FIG. 13, a further outer insulating layer 66 has been provided on top of exposed portion 30 and contiguous with outer layer 22. Thus, a void 68 is formed underneath annular layer 66 and above first conductor 18. As shown in FIG. 14, a electrode lead can thus be provided with a plurality of such regions 66 and corresponding voids 68 spaced at regular intervals so that first conductor 18 can readily be exposed at whichever point is expedient. In use, a physician can easily locate region 66 and quickly remove it, thereby exposing first conductor 18 for facilitating electrical connection in one of the aforedescribed methods. To enable ease in locating regions 66, marker lines 70 can be provided along the edges between each region 66 and the adjacent outer layer 22, for example.

Figure 15:
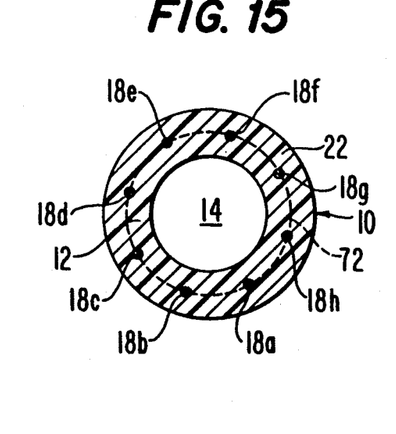
FIG. 15 is a cross-sectional view of a multiconductor electrode lead usable with the present invention according to a further embodiment.

FIG. 15 illustrates a further embodiment of a multi-conductor lead according to the present invention. In this embodiment, a plurality of conductors 18a-18h are disposed parallel to each other and aligned with the longitudinal axis of lead 10. First and second insulating layers 12 and 18 are effectively joined so as to encapsulate fully conductors 18a-18h. According to the invention, an annular portion of outer insulating layer 22 is selectively removed to a level as indicated by the dashed line in FIG. 15, thereby exposing conductors 18a-18h for contact with surrounding tissues or for electrical connection in a manner as described previously with respect to the embodiments shown in FIGS. 1-14.

While eight conductors have been illustrated in FIG. 15, it should be appreciated that more or fewer conductors may be used. Further, the conductors can either be connected to a common source or to different sources individually or to any combination thereof. All of these changes are considered to be within the spirit and scope of the present invention.

From the foregoing, it should be appreciated that an implantable electrode lead according to the present invention provides for connection to an inner conductor without markedly increasing the diameter of the electrode lead so as to make implantation difficult. It will be apparent to those skilled in the art that modifications and variations can be made in the electrode lead apparatus of thus invention. The invention in its broader aspects is, therefore, not limited to the specific details, representative methods and apparatus, and illustrate examples shown and described above. Thus, it is intended that all matter contained in the foregoing description or shown in the accompanying drawings shall be interpreted as illustrative and not in a limiting sense.

What is claimed is:

1. A body implantable electrode lead, comprising:
   a first layer of non-conductive material forming an elongated tube;
   an intermediate layer of non-conductive material disposed coaxially about said first layer;
   a conductor disposed about said first layer and imbedded within said intermediate layer, the conductor being regularly disposed about said first layer and comprising a first conductor;
   a second layer of body-compatible non-conductive material formed over said first conductor, said intermediate layer and said first layer, with an annular portion of said second layer and said intermediate layer having been eliminated to expose a section of said regularly disposed first conductor and facilitate electrical connection therewith;
   a second conductor provided coaxially about said exposed section of said regularly disposed first conductor, said second conductor effectively forming a conductive ring; and
   a conductive adhesive interposed between said regularly disposed first conductor and said conductive ring for electrically and mechanically coupling said conductive ring to said regularly disposed first conductor.

2. A body implantable electrode lead as recited in claim 1, wherein said conductive ring is positioned coaxially over said exposed section of said first conductor and over edges of said second layer adjacent said exposed section.

3. A body implantable electrode lead as recited in claim 2, wherein said ring has a pair of opposed holes through which said conductive adhesive can be injected after said ring is positioned over said first conductor.

4. A body implantable electrode leas as recited in claim 2, wherein said ring is secured to said second layer via a biocompatible adhesive.

5. A body implantable electrode lead as recited in claim 1, wherein said first layer encloses an inner helically wound conductor, said electrode lead thus being bipolar.

6. A body implantable electrode lead as recited in claim 5, wherein the lead has a proximal end including a plug-like connector, said connector being coupled to said conductive ring via said first conductor.

7. A body implantable electrode lead as recited in claim 5, wherein the lead has a distal end having an implantable distal tip electrode including said conductive ring.

* * * * *